US010967085B1

(12) United States Patent
Gaskins et al.

(10) Patent No.: US 10,967,085 B1
(45) Date of Patent: Apr. 6, 2021

(54) APPARATUS AND METHOD FOR DISINFECTING ENTITIES

(71) Applicant: Project Pure Life LLC, Naples, FL (US)

(72) Inventors: Craig Gaskins, Naples, FL (US); Barry Connor, Naples, FL (US)

(73) Assignee: Project Pure Life LLC, Naples, FL (US)

( * ) Notice: Subject to any disclaimer, the term of this patent is extended or adjusted under 35 U.S.C. 154(b) by 0 days.

(21) Appl. No.: 16/984,425

(22) Filed: Aug. 4, 2020

Related U.S. Application Data

(63) Continuation of application No. 16/879,057, filed on May 20, 2020, now abandoned.

(60) Provisional application No. 63/000,573, filed on Mar. 27, 2020.

(51) Int. Cl.
*A61L 2/22* (2006.01)

(52) U.S. Cl.
CPC ............ *A61L 2/22* (2013.01); *A61L 2202/11* (2013.01); *A61L 2202/121* (2013.01); *A61L 2202/122* (2013.01); *A61L 2202/14* (2013.01); *A61L 2202/15* (2013.01); *A61L 2202/20* (2013.01)

(58) Field of Classification Search
CPC .... A61L 2/22; A61L 2202/14; A61L 2202/20; A61L 2202/122; A61L 2202/11; A61L 2202/121; A61L 2202/15
See application file for complete search history.

(56) References Cited

U.S. PATENT DOCUMENTS

| 8,303,905 | B2 | 11/2012 | Brents et al. | |
|---|---|---|---|---|
| 2005/0110672 | A1* | 5/2005 | Cardiasmenos | ... G01N 21/3581 342/27 |
| 2016/0179089 | A1* | 6/2016 | Stratmann | ............... E05F 15/70 700/231 |
| 2016/0339132 | A1* | 11/2016 | Cosman | .................... F26B 3/04 |
| 2018/0117194 | A1* | 5/2018 | Dobrinsky | ............... A61L 2/00 |
| 2019/0064342 | A1* | 2/2019 | Daisy | .................. G01N 23/046 |
| 2020/0134520 | A1* | 4/2020 | Kantor | .................. G06Q 10/06 |

FOREIGN PATENT DOCUMENTS

GB  2545685  *  6/2017  ............... A61L 2/24

* cited by examiner

*Primary Examiner* — Sean E Conley
*Assistant Examiner* — Brendan A Hensel
(74) *Attorney, Agent, or Firm* — Laubscher & Laubscher, P.C.

(57) ABSTRACT

A health and safety apparatus for entities such as individuals or objects includes a housing containing at least one side opening, a plurality of fluid atomizing dispensers, and a reservoir containing a fluid which includes a sanitizer, sterilizer or disinfectant. The housing includes a top wall and at least one side wall defining an inner chamber. The dispensers are mounted in spaced relation on the top and side walls and are connected with the reservoir. When an entity is arranged in the housing, the atomizing dispensers are activated to spray the fluid onto the entity. In a preferred embodiment, the housing further includes a bottom wall configured for collecting fluid. Preferably, the apparatus includes at least one motion sensor mounted on the housing for detecting motion at a threshold of the side opening to electronically operate the atomizing dispensers for a defined period of time.

5 Claims, 5 Drawing Sheets

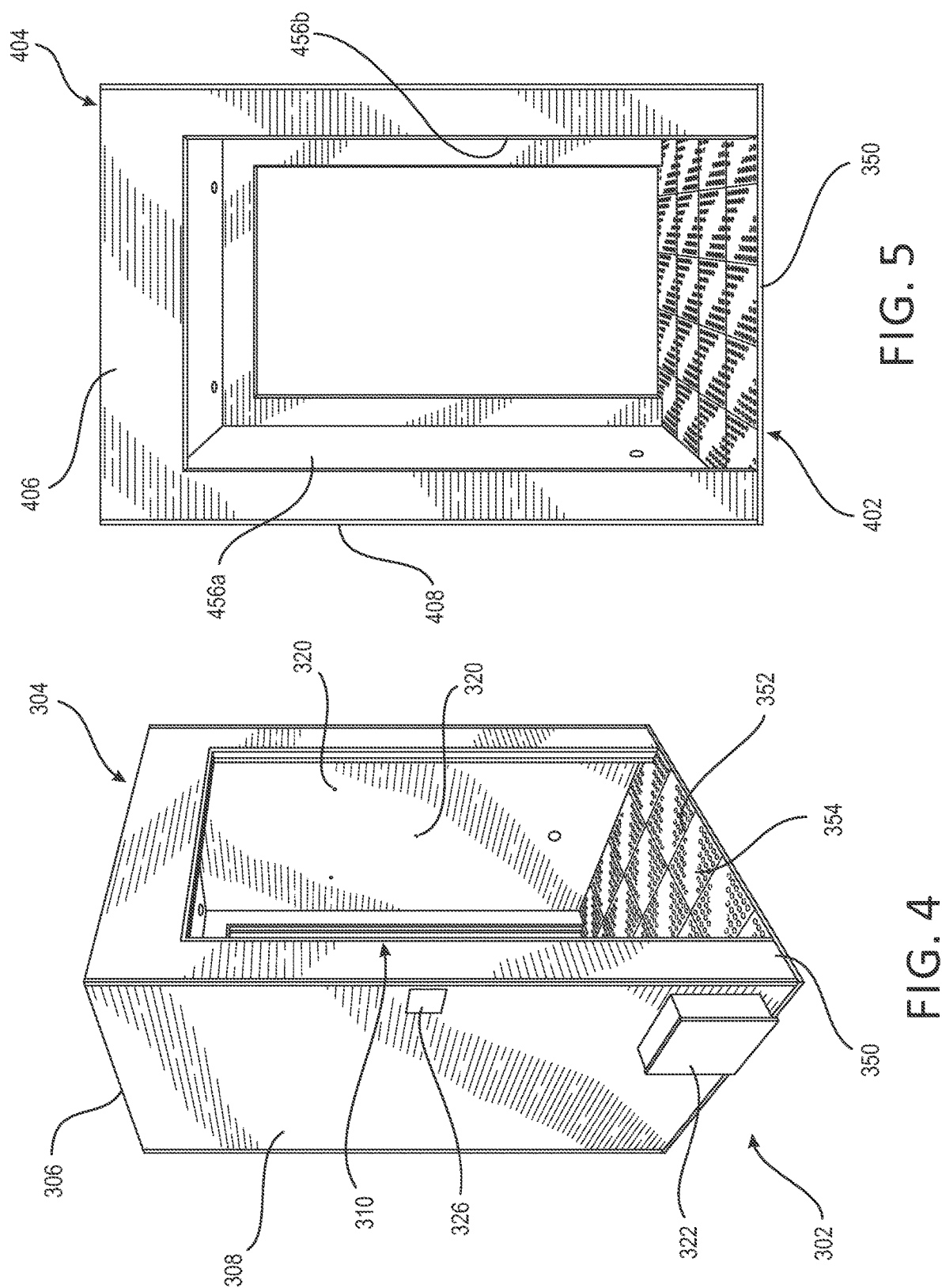

APPARATUS AND METHOD FOR DISINFECTING ENTITIES

This application claims the benefit of U.S. provisional patent application No. 63/000,573 filed Mar. 27, 2020, and is a continuation of U.S. patent application Ser. No. 16/879, 057 filed May 20, 2020.

BACKGROUND OF THE DISCLOSURE

The present disclosure relates generally to an apparatus designed for safe and healthy entry to a building or space, and more specifically to an enclosure designed for safe and healthy entry to a building or space.

A wide range of apparatuses are used to provide safe and healthy entry into buildings and/or spaces. Chemicals are used with many methods of application to disinfect individuals and objects. Such methods might include using liquid sanitizers, wipes, or sprays, to name a few. Most sanitizing dispensers treat hard surfaces and hands while many pathogens can be transmitted via hair, clothing, mobile phones, handbags, shoes, or other objects. To provide more comprehensive disinfecting, mists and fogs are used in an attempt to sanitize an entire body of an individual or object.

Beyond the use of disinfectants, metal detectors are often used at the entry of a building or space to detect if individuals have weapons or other such devices on their person. In some instances, for example in airports, millimeter wave scanners are used to detect concealed objects. Other devices, such as thermal imaging, also provide a method for detect concealed object. These and other such devices are often used to ensure safe entry to a building or space.

BRIEF DESCRIPTION OF THE PRIOR ART

One example of a misting device is disclosed in the Warren UK Patent Application No. GB 2,545,685, which discloses an apparatus for killing pathogens that includes an enclosed chamber. A person or people enter and remain in the chamber for a predetermined period of time while a fine mist containing a chemical is released to kill pathogens on exposed surfaces, such as a person's hair, skin, clothing and personal effects. The entire process is activated by a person offering his or her hand to a sanitizing dispenser, at which time the apparatus automatically begins the process of releasing the fine mist. The mist is dispensed via a mist generator and fan.

There are concerns with current devices and methods that include fogs or mists for killing pathogens, such as described above, because most provide varying degrees of effectiveness. Sufficiently disinfecting the entire body of an individual or object with such devices and methods is difficult. Further, when used in public spaces such as offices, government buildings, airports and the like, a fogging or misting machine adds another device and step in the process of safely entering a building or space.

Accordingly, there is a need for a device that sufficiently disinfects the entire body of an individual or object, and also can be incorporated with, or includes, other devices and methods used to provide for a safe and healthy means of entering a space or building.

SUMMARY OF THE DISCLOSURE

Accordingly, it is an object of the present disclosure to provide a health and safety apparatus for entities such as individuals and objects, which includes a housing containing at least one side opening, a plurality of fluid atomizing dispensers, and a reservoir containing a fluid which includes a sanitizer, sterilizer or disinfectant. The housing includes a top wall and at least one side wall defining an inner chamber. The plurality of dispensers are mounted in spaced relation to the top and side walls and are connected with the reservoir. When an individual or object is arranged in the housing, the plurality of atomizing dispensers are activated to spray the fluid onto the entity. In a preferred embodiment, the housing further includes a bottom wall configured for collecting fluid. Preferably, the apparatus includes at least one motion sensor mounted on the housing for detecting motion at a threshold of the side opening to electronically operate the plurality of atomizing dispensers for a defined period of time.

In another embodiment, the apparatus includes an actuator connected with the plurality of atomizing dispensers for manually operating the dispensers. Preferably, the actuator is triggered by a proximity sensor and/or a foot pedal.

In yet another embodiment, the housing includes at least one metal sensor arranged along edges of the top wall and side walls and a temperature sensor mounted to the housing. The metal sensor is configured to detect metal at a threshold of the side opening, and the temperature sensor is configured for detecting the temperature of an entity.

In a further embodiment, the apparatus includes a plurality of ultraviolet lights and a movable wall. The lights are mounted in spaced relation on the housing side and top walls, and the moveable wall is for selectively closing the side opening.

In another embodiment, the side walls include millimeter wave scanner panels which are used to detect concealed objects of an individual or object.

It is also an object of the present disclosure to provide a method for disinfecting individuals via a housing which includes fluid dispensers and motion, metal and temperature sensors. The method includes the steps of sensing motion when an individual approaches the housing, measuring the temperature of the entity, prompting the individual to enter the compartment, detecting metal on the individual when the individual enters the housing, releasing an atomized fluid disinfectant for a defined period, and prompting the individual to exit the housing.

In one embodiment, the method further includes prompting the individual to turn toward a sidewall of the housing to maintain a specified position.

In another embodiment, the method further includes operating a plurality of ultraviolet lights for a defined period after the individual has entered the housing.

BRIEF DESCRIPTION OF THE FIGURES

Other objects and advantages of the disclosure will become apparent from a study of the following specification when viewed in the light of the accompanying drawing, in which:

FIG. 4 is a perspective view of a fourth embodiment of an apparatus for disinfecting entities according to the present disclosure;

FIG. 5 is a front view of a fifth embodiment of an apparatus for disinfecting entities according to the present disclosure.

DETAILED DESCRIPTION

The present disclosure relates to a system or apparatus for disinfecting entities such as individuals and objects, as well as for detecting concealed objects and measuring the temperature of an individual or object. The apparatus is similar to a booth, kiosk or other structure which contains an inner chamber in which an individual can stand, or an object can be placed.

Figure 1:
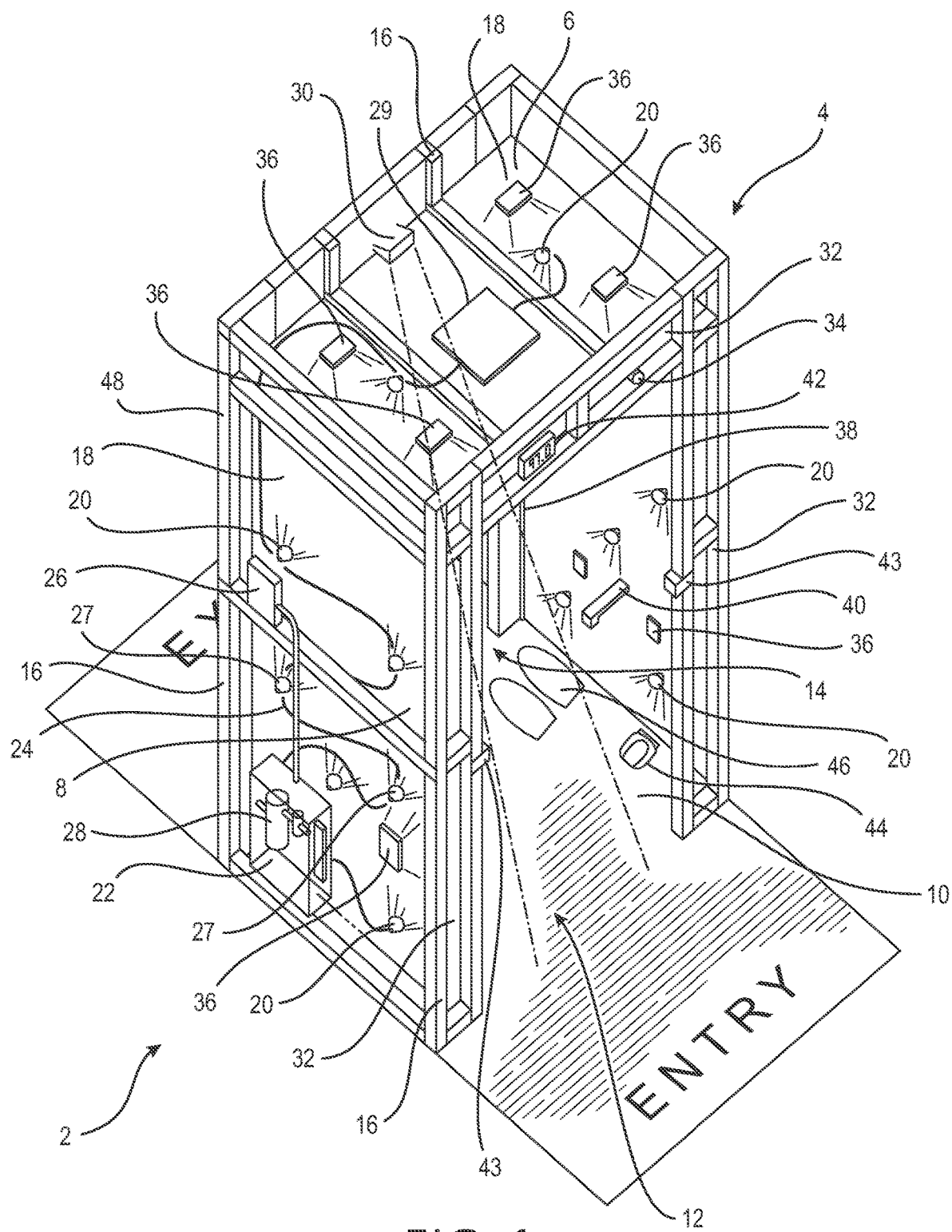
FIG. 1 is a top perspective view of an apparatus for disinfecting entities according to the present disclosure.

Referring first to FIG. 1, the apparatus 2 includes a housing 4 with a top wall 6 and two side walls 8 defining an inner chamber 10. The inner chamber is accessed via a front opening 12 and a rear opening 14 positioned opposite the front opening. The housing includes a metal frame 16 and wall panels 18. FIG. 1 shows the inner wall panels but does not show the outer wall panels in order to expose inner compartments of the frame to show the devices related to the function of the apparatus.

There are a plurality of fluid atomizing dispensers 20 mounted in spaced relation on the side 8 and top 6 walls, and a reservoir 22 containing a fluid for disinfecting individuals and objects mounted on a side wall. On the side wall opposite that with the reservoir, there is a second reservoir (not shown) which includes a self-cleaning formula for cleaning the inner chamber of the housing. The reservoir is connected with the dispensers 20 via an outlet line 24 which provides the fluid to the dispensers and is connected with a controller 26 which operates a pump 28 connected with the reservoir. The pump is operated to send fluid that is in the reservoir to the dispensers. The fluid in the reservoir preferably includes at least one of a sanitizer, sterilizer and disinfectant. There are also a pair of hand nozzles 27 which provide direct sanitization of an individual's hands via mist or fog, and an air-blade vortex fan 29 to circulate air within the chamber which increases the coverage of the disinfectant on an individual or object.

In addition to the dispensers, other options for the system include a motion sensor 30 mounted on the top wall 6, which is also connected with the controller 26. The motion sensor is configured to sense motion at the threshold of the housing front opening 12. There is also a metal detecting loop 32 arranged within edges of the side 8 and top 6 walls, a temperature sensor 34 arranged at a forward edge of the top wall, light-emitting diodes (LEDs) 36 and ultraviolet (UV) lights 38 mounted on the housing, and a sanitizing wand 40 also mounted on the housing.

When an individual or object approaches the housing 4, the motion sensor 30 detects motion and sends a signal to the controller 26 which causes the devices of the system to begin operating. The temperature sensor 34 measures the temperature of the individual, which is shown on the display 42 mounted on the top wall 6. The individual is then signaled to enter the housing via an audio or visual prompting, such as prerecorded directions, lights, or another method for prompting the individual.

While crossing the threshold of the front opening 12, the metal detecting loop 32 detects any metal that is on an individual or object. A proximity reader 43 detects when the individual or object enters the housing 4, at which time the controller 26 operates the reservoir pump 28 and fluid is dispensed as a mist or fog to the inner chamber for a set period of time. This can be done automatically by having the motion sensor signal the controller when the individual or object enters the housing. Alternatively, there is a foot pedal 44 for manually engaging the controller to operate the pump. Following the application of mist/fog, the individual or object waits to exit the housing until prompted to do so. This allows for drying of the mist/fog prior to exiting. There is also a foot or shoe disinfecting station 46 which disinfects the soles of an individual's feet or shoes if desired.

As noted above, there are audio or visual signals to prompt an individual or object during the process described above. For instance, there might be a light prompting system similar to that of traffic signals, including red, yellow and green lights. The red light remains on while an entity is in the housing and disinfectant is being applied. Once the disinfectant is applied, the red light turns off and a yellow light turns on to prompt the entity that the process is almost complete. The yellow light remains on while the entity dries. Once a set dry time has passed, the yellow light turns off and a green light turns on, prompting the user to exit the housing. The user can be further prompted to remain in the housing and subsequently to exit the housing via a gate arm 48, which is arranged in a horizontal position when the user should remain in the housing, then rotates to a vertical position signaling to the user that it is time to exit the housing.

Figure 2:
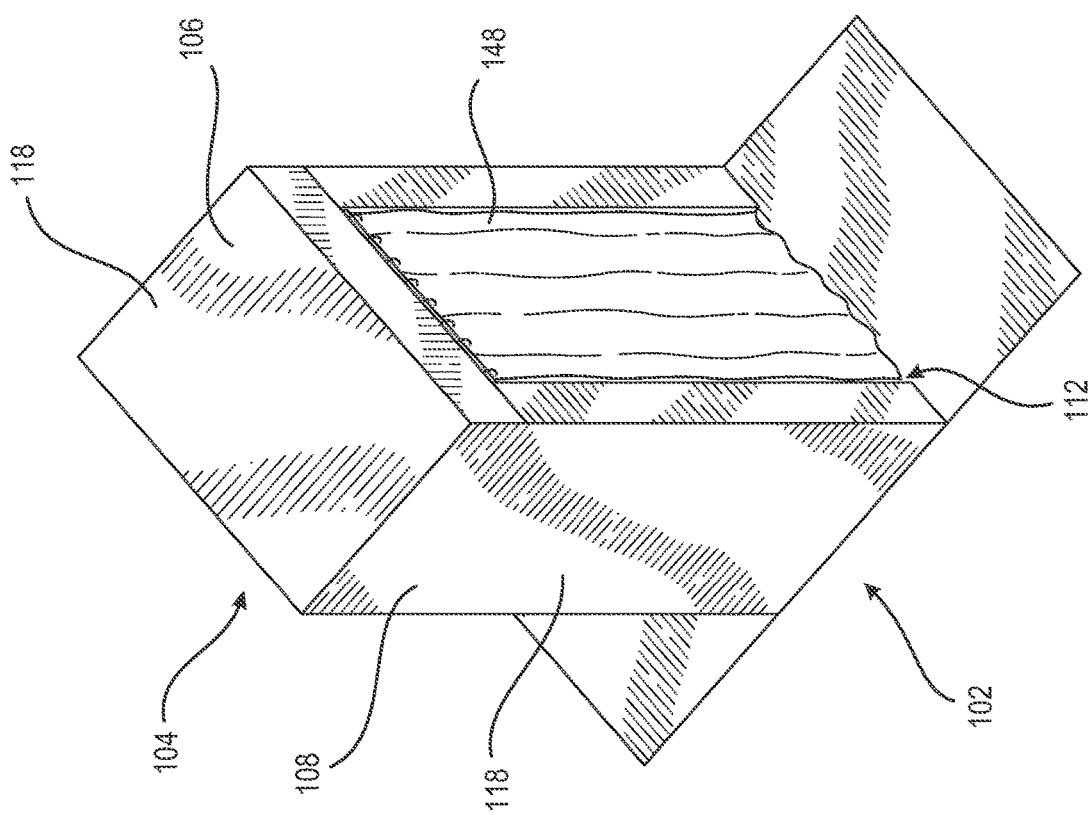

FIG. 2 shows an apparatus 102 that is similar to that of FIG. 1 but including the outer panels 118 of the side 108 and top 106 walls of the housing 104. Thus, unlike in FIG. 1, the components arranged within the frame compartments of the housing are not shown. The housing 104 of this embodiment further includes a moveable wall 148 which is used to selectively open or close the front opening 112. The movable wall provides for privacy of an entity and also assists in containing disinfectant mist or fog within the housing chamber. One example of such a moveable wall 148 is a curtain.

Figure 3:
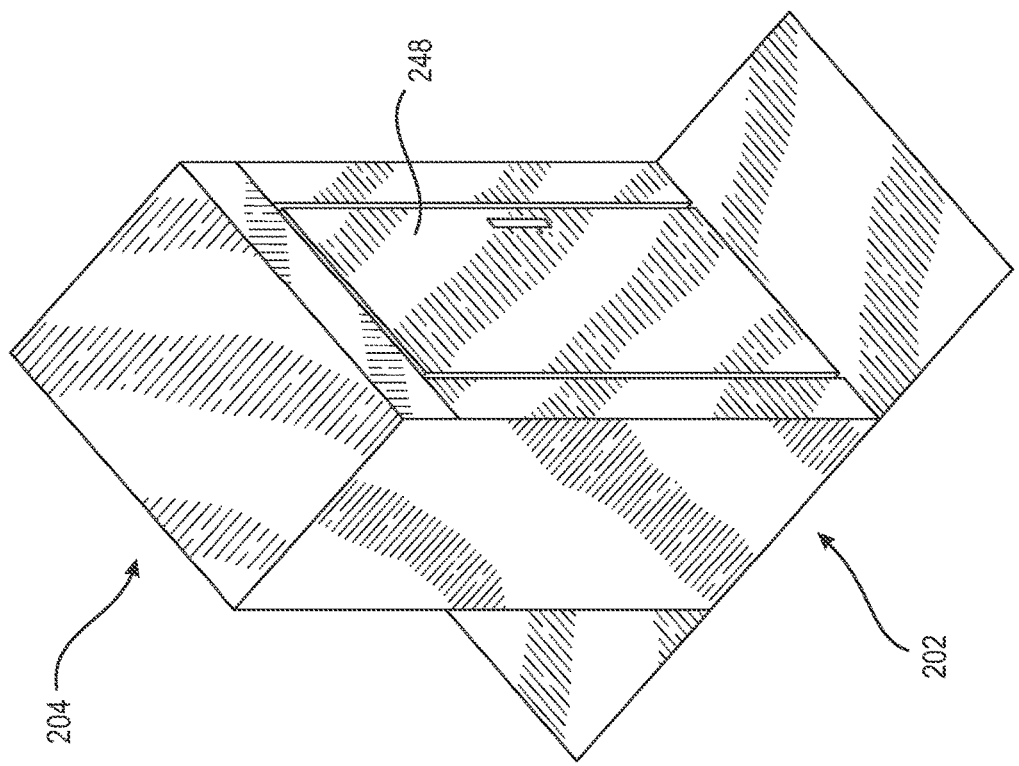
FIGS. 2 and 3 are top perspective views of second and third embodiments, respectively, of an apparatus for disinfecting entities according to the present disclosure.

FIG. 3 shows an apparatus 202 that is nearly identical to that of FIG. 2, but instead of the housing 204 having a curtain, the moveable wall 248 is a door. This adds an increased level of privacy and a more effective mechanism for containing disinfectant within the housing inner chamber. It will be understood by those will skill in the art that other movable walls can be included in the place of those shown in FIGS. 2 and 3.

FIG. 4 shows an additional embodiment of an apparatus 302 for disinfecting entities. Similar to those described above in FIGS. 1-3, this apparatus includes a housing 304 having a top wall 306 and two side walls 308 defining an inner chamber 310, a controller 326, a reservoir 322 and dispensers 320. In addition to those elements, there is a bottom wall 350 and a wall covering 352 containing uniformly spaced openings 354 through which fluid can pass. When the dispensers 320 release a mist or fog to disinfect an individual or object, excess mist or runoff from an entity passes through the openings 354 to the bottom wall 350 where it collects. The covering shown in FIG. 4 is a rubber mat. It will be understood by those will skill in the art that coverings made of other materials, such a metal or plastic can be used without deviating from the purpose or effectiveness of the covering.

The apparatus 402 of FIG. 5 is similar to that of FIG. 4 in that it includes a housing 404 having a top wall 406 and two side walls 408 as well as a bottom wall 450 as described above. The apparatus also includes other elements described in the aforementioned embodiments but not shown here, such as dispensers and a controller. In addition to those elements, the sidewalls of the housing include millimeter wave scanner panels for scanning individuals or objects.

Millimeter wave scanners are used in airports by the U.S. Transportation Security Administration (TSA) to ensure safe travel within the Unites States. There is a transmitter panel 456a with thousands of transmitter antennas that emit low-power millimeter waves in short succession, and a receiver panel 456b with receiver antennas. The scanners are connected with the processor and are used to detect concealed objects not otherwise detectable. To be scanned, an individual stands between the panels, faces one of the panels, and raises his or her arms slightly away from his or her body. The scan includes a frequency range of 70-80 gigahertz and requires approximately 16-32 milliseconds to complete.

Figure 6:
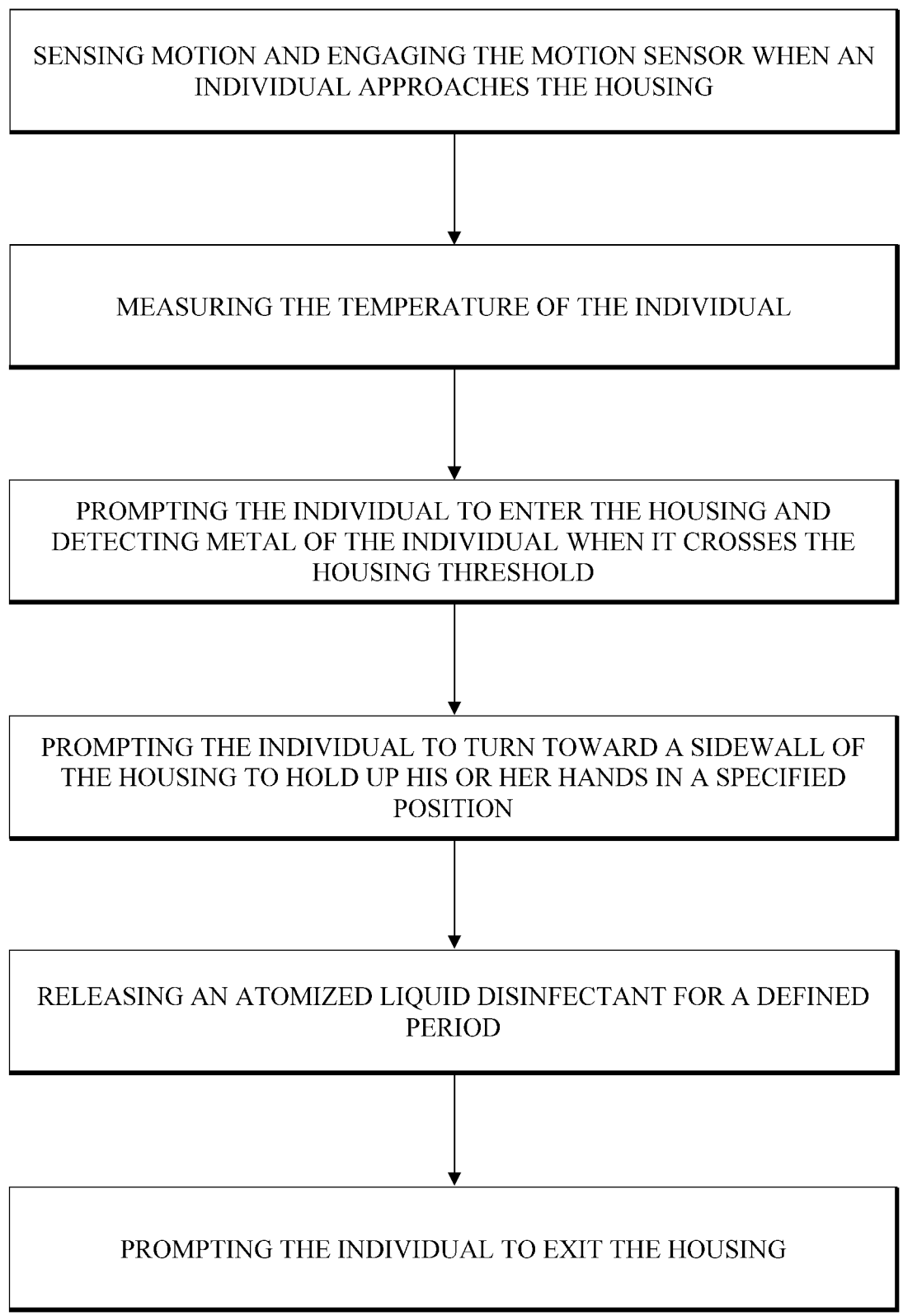
FIG. 6 is a flow chart of a method for disinfecting individuals according to the present disclosure.

Referring now to FIG. 6, a method for disinfecting individuals via a housing which includes dispensers and motion, metal and temperature sensors, is shown. The method includes the steps of, sensing motion when an individual approaches the housing, measuring the temperature of the individual, prompting the individual to enter the housing, detecting metal of the individual when the individual enters the housing, prompting the individual to turn toward a sidewall of the housing to maintain a specified position, releasing an atomized fluid disinfectant for a defined period, and prompting the individual to exit the housing.

Figure 7:
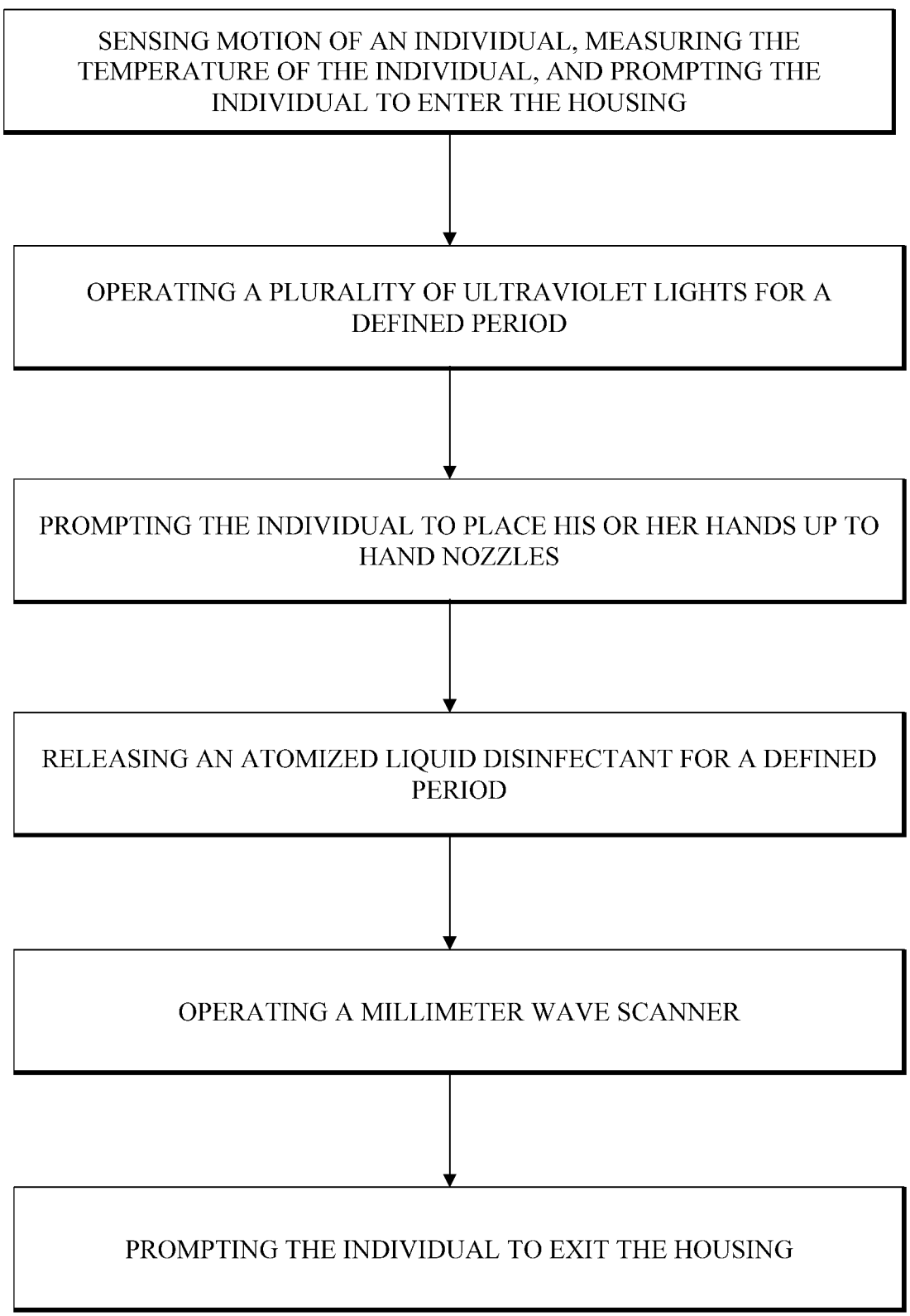
FIG. 7 is a flow chart of a method for disinfecting individuals according to the present disclosure.

FIG. 7 shows an alternate method which, in addition to sensing motion, measuring temperature, and prompting the individual to enter the housing, includes the steps of operating a plurality of ultraviolet lights for a defined period after the individual has entered the housing, prompting the individual to place his or her hands up to hand nozzles for disinfecting the individual's hands, and operating a millimeter wave scanner to detect concealed objects of the individual.

Although the above description references particular embodiments, it is to be understood that these embodiments are merely illustrative of the principles and applications of the present disclosure. It is therefore to be understood that numerous modifications may be made to the illustrative embodiments and that other arrangements may be devised and employed without departing from the spirit and scope of the present disclosure.

What is claimed is:

1. A method for reducing viral or bacterial spread and increasing security of a premises via a housing including disinfecting dispensers and motion, metal and temperature sensors, comprising the steps of:
   (a) sensing motion when an individual approaches the threshold of the housing;
   (b) automatically measuring and displaying the temperature of the individual at the threshold of the housing;
   (c) prompting the individual to enter the housing;
   (d) at least one of detecting metal near the individual when the individual enters the housing and operating a millimeter wave scanner to detect concealed objects of the individual after the individual has entered the housing;
   (e) releasing an atomized fluid disinfectant on the individual for a defined period after the individual has entered the housing; and
   (f) prompting the individual to exit the housing after the individual has remained in the housing for the defined period.

2. A method for reducing viral spread and increasing security of a premises as defined in claim 1, and further comprising the step of prompting the individual to place the individual's hands under a hand sanitizer nozzle to sanitize the individual's hands prior to prompting the individual to exit the housing.

3. A method for reducing viral spread and increasing security of a premises as defined in claim 1, wherein said operating a millimeter wave scanner step includes prompting the individual to turn toward a sidewall of the housing and maintain a specified position.

4. A method for reducing viral or bacterial spread and increasing security of a premises as defined in claim 1, and further comprising the step of operating a plurality of ultraviolet lights for a defined period after the individual has entered the housing.

5. A method for reducing viral or bacterial spread and increasing security of a premises via a housing including disinfecting dispensers and motion, metal and temperature sensors, comprising the steps of:
   (a) sensing motion when an individual approaches the threshold of the housing;
   (b) automatically measuring and displaying the temperature of the individual at the threshold of the housing;
   (c) prompting the individual to enter the housing;
   (d) detecting metal near the individual when the individual enters the housing;
   (e) releasing an atomized fluid disinfectant on the individual for a defined period after the individual has entered the housing via one of automatically initiating the release of fluid and disinfectant after the individual has entered the housing and the individual engaging a foot pedal to initiate the release of fluid and disinfectant;
   (f) prompting the individual to turn toward a sidewall of the housing and maintain a specified position;
   (g) operating a millimeter wave scanner to detect concealed objects of the individual following said detecting metal step;
   (h) prompting the individual to place the individual's hands under disinfectant nozzles and disinfecting the individual's hands following said releasing an atomized fluid disinfectant step; and
   (i) prompting the individual to exit the housing after the individual has remained in the housing for a defined period.

* * * * *